(12) United States Patent
Besse et al.

(10) Patent No.: US 9,668,737 B2
(45) Date of Patent: Jun. 6, 2017

(54) MEDICAL INSTRUMENT HAVING A CORKSCREW-LIKE CONNECTION ELEMENT

(71) Applicant: Karl Storz GmbH & Co. KG, Tuttlingen (DE)

(72) Inventors: Regis Besse, Guyancourt (FR); Yann Thouement, Les Essarts le Roi (FR); Sven Schneider, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 282 days.

(21) Appl. No.: 14/191,045

(22) Filed: Feb. 26, 2014

(65) Prior Publication Data

US 2014/0243803 A1 Aug. 28, 2014

(30) Foreign Application Priority Data

Feb. 26, 2013 (DE) ........................ 10 2013 101 874

(51) Int. Cl.
| | |
|---|---|
| *A61B 17/10* | (2006.01) |
| *A61B 17/076* | (2006.01) |
| *A61B 17/122* | (2006.01) |
| *A61B 17/128* | (2006.01) |
| *A61B 17/22* | (2006.01) |
| *A61B 17/29* | (2006.01) |
| *A61B 17/00* | (2006.01) |
| *A61B 17/12* | (2006.01) |
| *A61B 17/28* | (2006.01) |

(52) U.S. Cl.
CPC ...... *A61B 17/076* (2013.01); *A61B 17/00234* (2013.01); *A61B 17/122* (2013.01); *A61B 17/128* (2013.01); *A61B 17/22031* (2013.01); *A61B 17/29* (2013.01); *A61B 2017/00473* (2013.01); *A61B 2017/00477* (2013.01); *A61B 2017/1205* (2013.01); *A61B 2017/22035* (2013.01); *A61B 2017/2808* (2013.01); *A61B 2017/2931* (2013.01)

(58) Field of Classification Search
CPC . A61B 17/076; A61B 17/128; A61B 17/1285; A61B 17/0487; A61B 17/10; A61B 17/2804; A61B 17/2812; A61B 2017/0411; A61B 2017/049; A61B 2017/1205; A61B 2017/12054; A61B 2017/22035; A61B 2017/2931
See application file for complete search history.

(56) References Cited

U.S. PATENT DOCUMENTS

| 4,367,746 A * | 1/1983 | Derechinsky ...... A61B 17/1227 29/243.56 |
| 5,242,456 A | 9/1993 | Nash et al. |
| 5,437,266 A | 8/1995 | McPherson et al. |
| | (Continued) | |

FOREIGN PATENT DOCUMENTS

| WO | 9309721 A1 | 5/1993 |
| WO | 9511620 A2 | 5/1995 |
| WO | 9727808 A1 | 8/1997 |

*Primary Examiner* — Melaine Tyson
(74) *Attorney, Agent, or Firm* — Whitmyer IP Group LLC

(57) ABSTRACT

A medical instrument has two individual parts. The first individual part has an eyelet, which is provided with an edge fully surrounding the eyelet opening. A second individual part includes a corkscrew-like manner connection body having turns which are wound into the eyelet opening.

20 Claims, 8 Drawing Sheets

(56) References Cited

U.S. PATENT DOCUMENTS

| | | | |
|---|---|---|---|
| 5,496,333 | A | 3/1996 | Sackier et al. |
| 5,573,496 | A | 11/1996 | McPherson et al. |
| 5,749,881 | A | 5/1998 | Sackier et al. |
| 8,945,155 | B2 * | 2/2015 | Gordin .................... A61B 1/32 606/151 |
| 2001/0034536 | A1 | 10/2001 | Looper et al. |
| 2008/0221582 | A1 * | 9/2008 | Gia ...................... A61B 17/221 606/99 |
| 2009/0222029 | A1 | 9/2009 | Gordin et al. |
| 2012/0245598 | A1 | 9/2012 | Brown et al. |
| 2012/0253365 | A1 | 10/2012 | Sikora et al. |
| 2012/0296348 | A1 | 11/2012 | Saadat et al. |

* cited by examiner

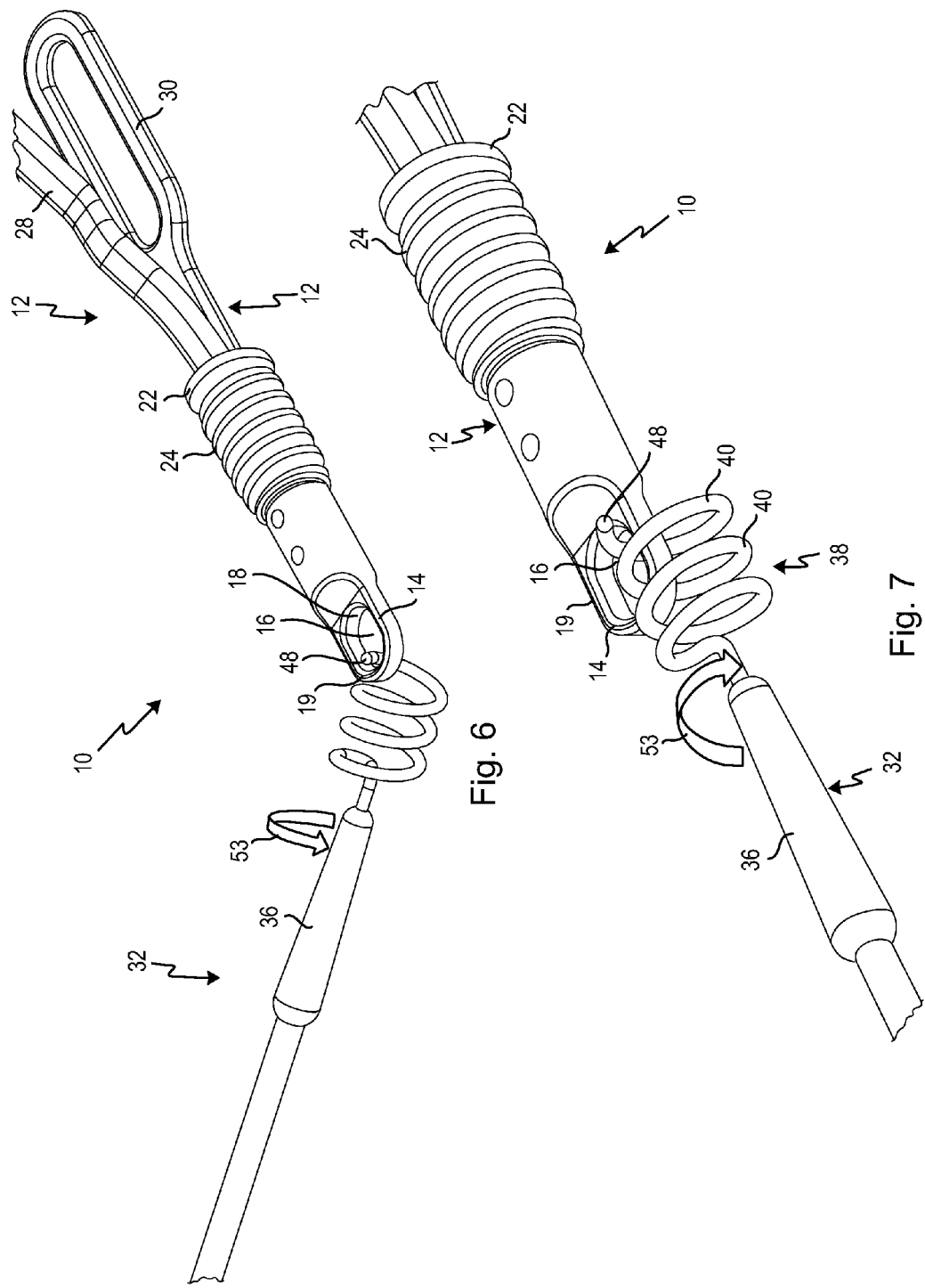

MEDICAL INSTRUMENT HAVING A CORKSCREW-LIKE CONNECTION ELEMENT

FIELD OF THE INVENTION

The invention relates to a medical instrument having two individual parts which can be releasably connected one to another via a hook/eyelet connection.

BACKGROUND OF THE INVENTION

A medical instrument of this type is known from U.S. Pat. No. 5,749,881A. With this medical instrument the first individual part consists of a clamp comprising two spreadable and closable jaws. An eyelet is provided at one end.

A connection to a second individual part can be made via this eyelet, by a hook which can engage in the eyelet. With some surgical techniques the clamp is placed in the body and for example pinches a vessel or an organ in an isolating manner. After the surgical intervention the clamp must be recovered. This is achieved using the second individual part. The connection between the two parts can be released by moving the hook out of the eyelet.

A similar medical instrument is known from U.S. Pat. No. 5,242,456A1.

An instrument is known from WO 97/27808 A1 which is used to remove blood clots in vessels. To this end, the instrument, at its distal end, comprises a spirally wound body, which can be driven into the blood clot or traps it, such that the blood clot trapped by the spiralled body can be removed from the vessel.

A hook/eyelet connection bears the risk that this connection releases during the manipulations. A hook can escape from the eyelet as a result of a movement like pulling, pushing or turning the assembly of the two parts.

Considerations that involve forming the hooks as carabiner hooks or as a type of pipe hook may indeed solve the problem of inadvertent release of the hook/eyelet connection. A disadvantage here however is that, in the case of such a carabiner hook, the closure of the carabiner has to be pressed in from the side so that the carabiner can exit from the eyelet.

Medical instruments are used within a living body, such that it is extremely difficult to open a corresponding carabiner hook or closure thereof in the body. In the case of minimally invasive surgery, the instruments are usually received in tubular hollow shafts. In this case, access to a lateral closure of a carabiner hook is practically impossible.

SUMMARY OF THE INVENTION

It is therefore an object of the present invention to create a releasable hook/eyelet-like connection between two individual parts that ensures, in the case of the routine handling measures, that this connection does not release accidentally.

The object is achieved by a medical instrument having two individual parts with a first individual part comprising an eyelet having an eyelet opening fully surrounded by an eyelet edge having a thickness, and a second individual part comprising a connection body inserted into said opening of said eyelet, said connection body having turns wound in a corkscrew-like manner about a longitudinal axis of the second individual part, said turns turning at a radial distance from said longitudinal axis and around said longitudinal axis, two adjacent turns having an axial distance from another corresponding at least to said thickness of said edge surrounding said eyelet, said turns of said connection body extending from a body of said second part, at least a section of one turn being screwed into said opening, said at least one turn engaging said eyelet provide a connection between said two individual parts which allow a pulling or a pushing of said connected two parts by pulling or pushing one of said two connecting parts, and allows a turning of said two parts in a direction of turning in of said connection body when said turns completely cross said eyelet opening.

These measures have the advantage that the connection is provided between the individual parts in that the connection body wound in a corkscrew-like manner is threaded via its free end into the eyelet, and, by rotating the connection body, a greater or lesser number of turns wind into or through the eyelet. Since the lead of the turns corresponds at least to the thickness of an edge surrounding the eyelet opening, this edge is received trapped between two turns, at the latest once one entire turn has been screwed in. Even in this state, a connection is created which cannot be released accidentally if the two individual parts are moved together in said axial direction or in twisted orientations. If so many turns are screwed into the eyelet such that the turns span the entire interior of the eyelet, a further rotation of the connection body will cause the first individual part to be rotated together with the second individual part. The eyelet is surrounded over the entire circumference by material and is usually worked out from this material. At least a portion of the edge surrounding the eyelet is formed with such a thickness that the turns can wind around this portion into the eyelet opening.

The connection can be easily released by rotating connection body wound in a corkscrew-like manner in the opposite direction, wherein the turns then wind out from the eyelet.

For the operator, these processes can be carried out easily and reliably. The threading process is routinely carried out under visual control during a minimal invasive interaction via an endoscope. The outermost turn of the connection body has an outer tip, via which it can be positioned at the eyelet, or this tip is inserted into the eyelet. By further rotating the connection body, an increasing number of turns wind into the eyelet opening. This continues until the turns span the entire opening, after which the connection body cannot be screwed in any further. This resistance is perceived by the operator, who then knows that the end position has been reached. No visual control is necessary for this. In this state, the assembly of the two individual parts can then be moved back and forth and also rotated in one direction.

If the connection has to be released, the second individual part has to be rotated in the opposite direction, such that the turns then wind out from the eyelet.

This connection between the individual parts is therefore suitable in particular for minimally invasive surgery, in which such processes and handling manoeuvres are performed in a hollow body or in relatively narrow body cavities.

If a clamp already placed in living body is to be recovered, merely the distal outer tip of the connection body has to be positioned at the eyelet, and the body can then be screwed in. If the clamp is to be recovered by pulling or if tissue is to be retracted, it is sufficient if only one or two turns are screwed into the eyelet, since this connection thus already reliably has strength.

In a further embodiment of the invention the connection body ends in an outer tip that runs approximately transversely to the longitudinal axis.

This measure has the advantage that the turns can be received in the eyelet in a particularly target-oriented and reliable manner. The tip, which extends approximately transversely to the longitudinal axis, can then be led accordingly to the eyelet from the side and can be threaded into the eyelet opening. This requires little space and can therefore be performed even in a hollow shaft of a minimally invasive instrument.

In a further embodiment the helix angle of the turns is less than 45°.

In further embodiments of the invention the helix angle lies in the range between 5° and 35°, most advantageously in the range between 10° and 20°.

The lower the helix angle, the less a turn rise from a plane transverse to the longitudinal axis. With a very low helix angle, it is sufficient if only one complete turn is screwed into the eyelet in order to already produce a reliable connection that has high strength.

If the eyelet has a very small opening, which is not much larger than the outer diameter of the body forming the turns of the connection body, a certain level of attention must be paid in order to thread the tip into such a small eyelet, however even a half rotation may be sufficient here with a small helix angle to create a connection that has high tensile strength, is shear-resistant and provides conjoint rotation.

If the eyelet is larger, it is easier to thread the tip of the connection body into the eyelet, however there is then space for a number of turns in the eyelet.

This may be intentional, since it is thus possible to pivot back and forth or to tilt the connection body relative to the eyelet, which may be desirable in some handling manoeuvres. If, for example, an eyelet of a clamp cannot be aimed directly in the longitudinal extension of the clamp, but the clamp can only be approached from the side due to the anatomical conditions, the turns can be threaded from the side into the eyelet and then aligned in a straight line by pulling on the second individual part, for example once the connection has been performed. In this alignment the two individual parts can be fed for example into a hollow shaft of a minimally invasive instrument and thus removed easily from the body.

This connection thus opens up a large number of possibilities for the design, on the one hand in order to be able to adapt to the respective local conditions, and on the other hand in order to make this connection reliable.

In a further embodiment of the invention the turns are each arranged at the same distance from the longitudinal axis, as considered over a portion of the longitudinal axis.

This measure has the advantage that the outer enveloping surface of the connection body is cylindrical, such that guidance along the inner wall of a tubular hollow shaft is possible very effectively during the back-and-forth movement.

In a further embodiment of the invention the outer diameters of the first individual part and of the second individual part are matched to one another in such a way that, in the connected state, both individual parts can be received in a hollow shaft suitable for minimally invasive surgery.

In a further embodiment of the invention the turns are formed from a wire having constant material diameter.

The wire material firstly allows a simple production of the connection body, wound in a corkscrew-like manner, as a result of a winding process around a core. The constant material diameter ensures that a connection body that is similarly steady over its entire length is produced.

In a further embodiment of the invention the first individual part, at one end, comprises a clamp which has spreadable jaws, whereas the eyelet is provided at the opposite end.

As already mentioned, such individual parts are often used in surgical interventions, and clamps of this type have to be moved, that is to say spread and opened, and can also be recovered again from the body.

In a further embodiment of the invention the jaws close as the first individual part is drawn into a hollow shaft, and the first individual part is movable by means of the second individual part in the hollow shaft.

Due to the tensile strength of the connection, the first individual part can be drawn into a hollow shaft via the second individual part due to the connection to the connection body wound in a corkscrew-like manner, whereby the jaws spread over the diameter of the hollow shaft close. For example, this assembly can be introduced minimally invasively in this state into a body. The second individual part can then slide the first individual part distally beyond the hollow shaft, wherein the jaws then spread again and can be positioned at a vessel or a tissue part to be gripped. If this assembly then moves back in the opposite direction, that is to say is drawn into the hollow shaft, the jaws close again. If, for example, the jaws are to remain in this state for a relatively long period of time during an intervention, the connection body wound in a corkscrew-like manner can be unscrewed from the eyelet and removed. The eyelet can then be re-entered at a later moment in time, and the connection closed again, for example in order to recover the clamp.

In a further embodiment of the invention the eyelet is surrounded at least over half of its outer circumference by the edge portion having said thickness.

The turns have to be able to enter the eyelet such that the eyelet geometry and the connection body wound in a corkscrew-like manner must match to a certain extent. To this end, it is sufficient however for this edge portion to surround the eyelet over half of the outer circumference thereof with a thickness of at least the axial distance between two adjacent turns. This portion is generally sufficient in order to position the turns and thread these into the eyelet. This means that, at the opposite end, the edge for example may then be much thicker, for example a rod-shaped body, the eyelet being worked out at the end area thereof.

In a further embodiment the edge of the eyelet has different thicknesses or depths.

Then, the turns can only be screwed in at specific thin edge portion points provided for this purpose.

In a further embodiment of the invention the outer circumferential edge portion is formed as a U-shaped bow.

This measure has the advantage that an oval-shaped, for example flat oval-shaped, eyelet opening of a specific length is thus provided. The connection body wound in a corkscrew-like manner can then be positioned laterally in a manner matched accordingly to the geometry, and a specific number of turns can be screwed in. As mentioned before, there is a relatively high degree of freedom by which a connection body screwed into the eyelet can be pivoted back and forth. This can be utilized to form the connection or the U-shaped bow as flat iron, such that, with corresponding angling, even the assembly can be rotated into an accordingly pivoted state in the direction in which the turns would normally be unscrewed. In other words, the connection body that has entered over a number of turns can be canted as a result of a corresponding pivot motion, such that the assembly can also be rotated in the direction in which the wire body can actually be unscrewed. Due to the clamping, an unscrewing process can then only be implemented however if the connection body is then realigned accordingly.

It is thus possible to produce the connection so as to provide conjoint rotation in both directions.

In a further embodiment the size of the eyelet opening is selected in such a way that in each case only one turn or few turns can be threaded in.

A reliable connection is thus created that allows, however, a high number of possibilities for angling and pivoting the connected individual parts relative to one another.

Of course, the features specified above and yet to be explained hereinafter can be used not only in the specified combinations, but also in other combinations or in isolation, without departing from the scope of the present invention.

BRIEF DESCRIPTION OF THE DRAWINGS

Exemplary embodiments of the invention are illustrated in the drawing and will be explained in greater detail in the following description. In the drawing:

FIG. 6 shows a state when producing the connection between the two individual parts, wherein the tip of the connection body of the second individual part has just been screwed into the eyelet of the first individual part, FIG. 7 shows an illustration in accordance with which a number of turns have been screwed in.

DETAILED DESCRIPTION OF THE INVENTION

Figure 1:
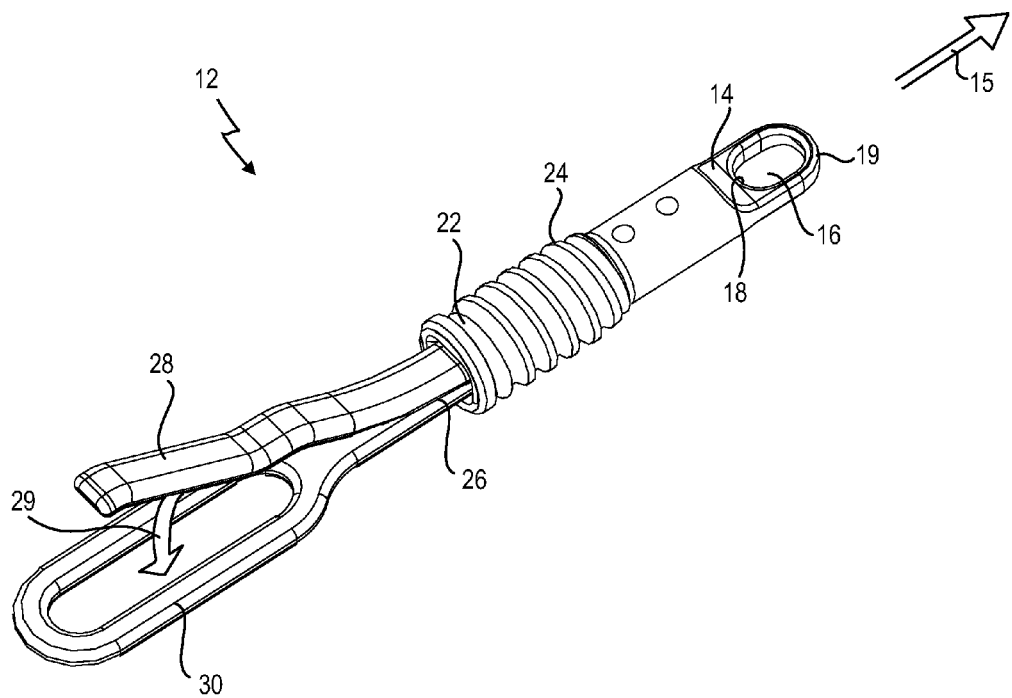
FIG. 1 shows a perspective view of an exemplary embodiment of a first individual part of the medical instrument according to the invention with the eyelet, the first individual part being formed as a clamp comprising two jaws, which are spread in FIG. 1.
Figure 2:
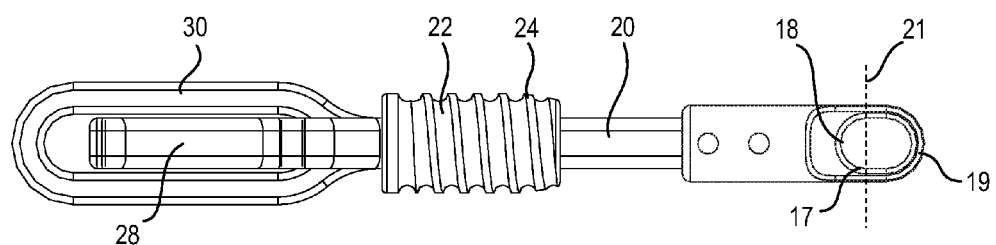
FIG. 2 shows a plan view of the clamp form FIG. 1 in a state in which the two jaws are closed.

A first individual part 12 of the medical instrument is shown in FIGS. 1 and 2.

The first individual part 12 comprises, at one end, an eyelet 14 having an eyelet opening 16.

As can be seen in particular from FIG. 2, the eyelet opening 16 consists of an elongate flat oval 17. The eyelet opening 16 is surrounded over the entire circumference by an edge 18. At least at its outer end, the eyelet opening 16 is surrounded by an edge portion 19, which, starting from a virtual dashed line 21 in FIG. 2, is formed as a U-shaped bow with branches running in a straight line.

The eyelet 14 transitions into a rod-shaped body 20, on which a sleeve 22 having an outer thread 24 is received in a slidable manner.

At the end opposite to the eyelet 14, the first individual part 12 is designed as a clamp 26 comprising two jaws 28 and 30.

Here, the jaw 30 extends in a median longitudinal plane of the first individual part 12, the second jaw 28 protruding upwardly from said plane.

The jaw 28 is pretensioned here with respect to the jaw 30, such that, in the position of FIG. 1, it protrudes upwardly from the jaw 30. If the instrument is pulled at the eyelet 14 in a direction as illustrated by the arrow 15 in FIG. 1, and if the sleeve 22 is screwed fixedly into a further individual part, the two jaws 28 and 30 of the clamp 26 are thus drawn into the sleeve 22. In so doing, the sleeve 22 presses the upwardly protruding jaw 28 downwards, as is illustrated in FIG. 1 by an arrow 29. An object, for example a piece of tissue or a vein, present between the jaws 28 and 30 is thus held or clamped.

It can be seen that the jaw 30 is formed as a hollow oval, such that the tab-shaped jaw 28 can penetrate into the hollow oval from one direction and thus not only tightly hold, but also similarly pinch in an isolating manner a vein or the like, for example.

The embodiment described here of the clamp 26 is just one example. Clamps that have two movable jaws can also be used. Clamps that are pretensioned into a closing position can also be used. These clamp a tissue when deposited on a tissue. Depending on the embodiment, these clamps open when handled or, along with the gripped tissue, can be moved or recovered from the body.

Individual parts 12 of this type therefore have to be moved back and forth for the manipulation thereof, for which purpose they are connected to a further individual part, which constitutes a connection via the eyelet 14.

Figure 3:
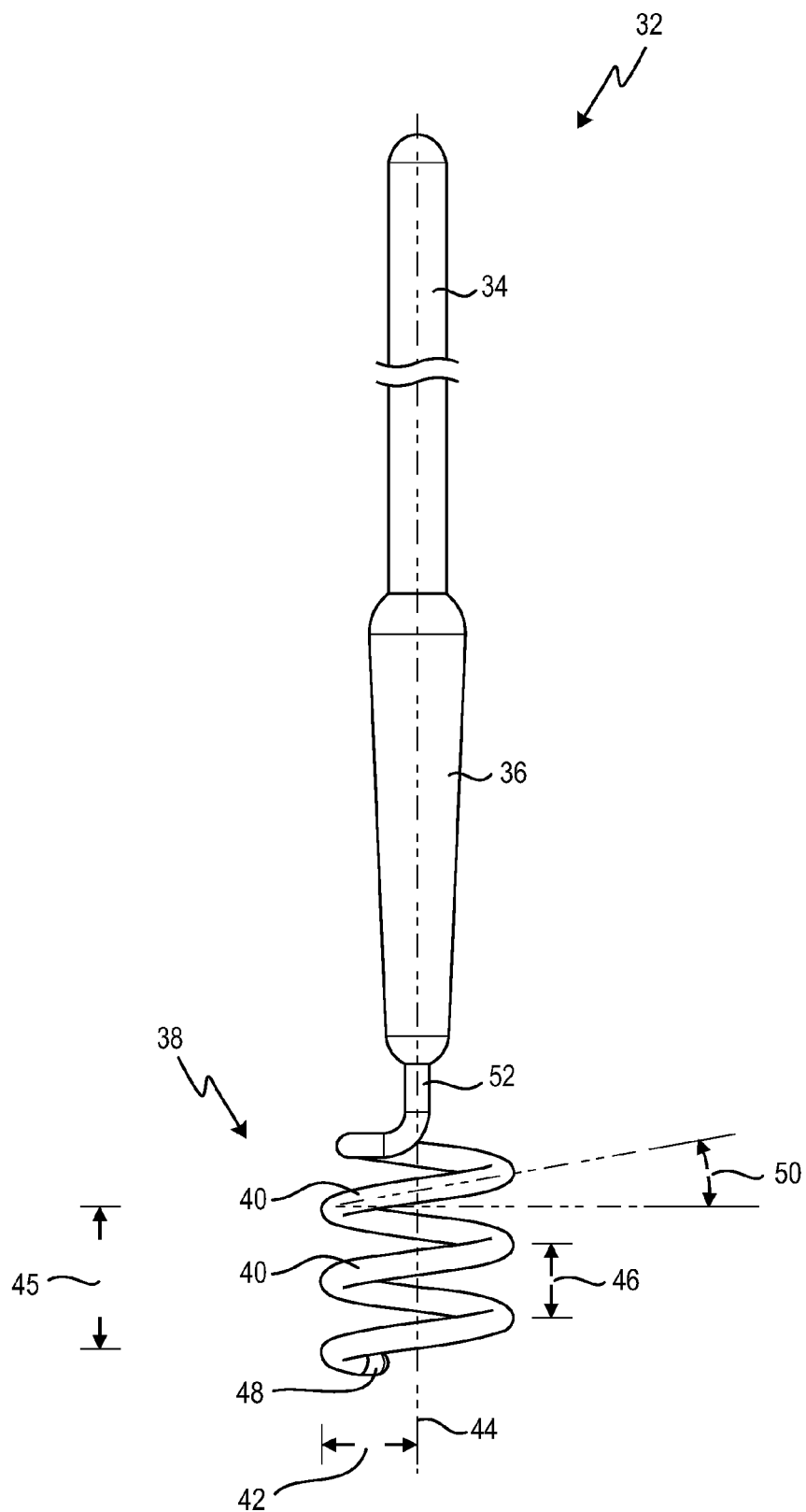
FIG. 3 shows a side view of a second individual part of the medical instrument according to the invention with a connection body wound in a corkscrew-like manner.
Figure 4:
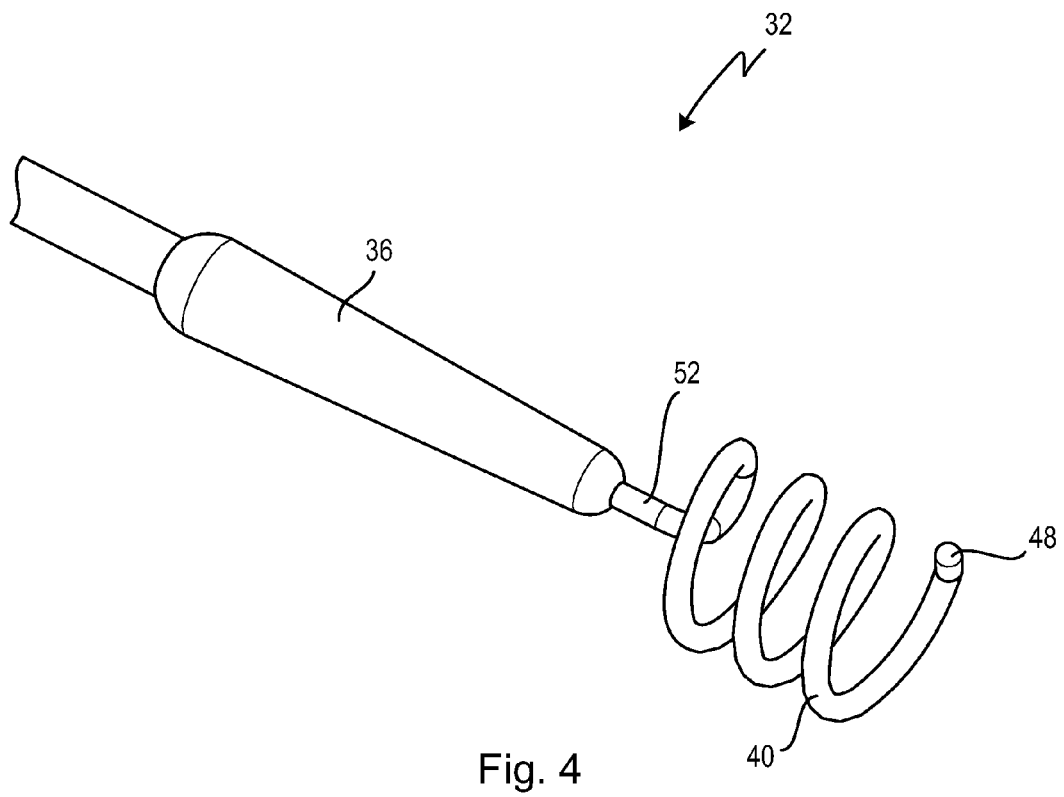
FIG. 4 shows a perspective view of the body from FIG. 3.
Figure 5:
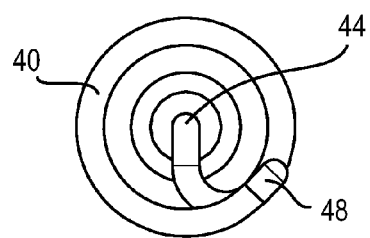
FIG. 5 shows a plan view from the end face of the body from FIGS. 3 and 4.

Such a second individual part 32 is illustrated in FIGS. 3 to 5.

The second individual part 32 has an elongate rod-shaped shaft 34, which transitions at one end into a slightly widened, conically tapering shaft portion 36.

A connection body 38 protrudes from the outer end of the shaft portion 36 and serves to produce a connection to the previously described eyelet 14 of the first individual part 12.

The connection body 38 consists of a body which is wound in a cork-screw-like manner and which has a number of turns 40. The turns 40 are designed such that they wind at a distance 42 around a central longitudinal axis 44 of the second individual part 32. The turns 40 are arranged of the same distance 42, at least over a portion 45, such that the connection body 38, if an outer enveloping surface around the turns 40 is visualized, has a cylindrical outer enveloping contour at least in the portion 45.

The lead 46, i.e. the axial distance between two adjacent turns is selected such that it corresponds at least to the thickness of the edge portion 19 of the previously described eyelet 14.

The helix angle 50 is approximately 10°.

The connection body 38 consists of a metal wire 52, which, starting from the outer end of the shaft portion 36, is shaped to form this spiralled connection body 38.

At the outer end, the connection body 38 ends in a tip 48 that extends in a plane, as is visible in particular from FIGS. 4 and 5, which runs approximately transversely to the median longitudinal axis 44. The tip 48 constitutes a rounded end of the wire 52.

FIGS. 6 and 7 now illustrate how the connection is produced between the eyelet 14 of the first individual part 12 and the connection body 38 of the second individual part 32 to form the medical instrument 10.

It can be seen from FIG. 6 that the tip 48 of the connection body 38 is inserted into the eyelet opening 16, and that the second individual part 32 is then rotated such that the turns 40 wind into the eyelet 14, as can be seen from the transition from FIG. 6 to FIG. 7.

The spiralled helix of the connection body 38 is thus a right-handed helix, that is to say the connection body 38 or the turns 40 thereof is/are screwed into the eyelet opening 16 by turning the second individual part 32 in a clockwise direction, as illustrated in FIGS. 6 and 7 by an arrow 53.

In FIG. 7 a situation is illustrated in which approximately one-and-a-half turns 40 are screwed into the eyelet opening 16.

This is already sufficient to produce a reliable connection that has high pulling and pushing strength between the first individual part 12 and the second individual part 32.

If the connection boy 38 is screwed into the eyelet 14 until the tip 48 contacts the end of the eyelet opening 16 that is the leading end in the screw-in direction, the connection body 38 cannot screwed in any further. A further rotation would then cause a rotation of the second individual part 32, such that a connection for conjoint rotation is then also provided at least in this direction, at the latest in this state. This direction of rotation can be utilized for example in order to screw the first individual part 12 via the sleeve 22 thereof into another individual part.

It is also possible to selectively screw in the turns 40 such that only a single turn 40 is screwed into the eyelet opening 16 in each case. Once the tip 48 has been threaded in once, the position of the connection body 38 can be changed, such that, with a further rotation, the tip 48 runs past the outer face of the eyelet 14. Only a single turn 48 is then threaded in the eyelet opening 16. This alone guarantees a reliable connection between the individual parts, but leaves open significant possibilities for pivoting or angling between the connected individual parts.

To release the connection between the first individual part 12 and second individual part 32, the first individual part 12 is then rotated in an anticlockwise direction, such that the turns 40 are unscrewed again from the eyelet opening 16 of the eyelet 14.

If, as described previously in conjunction with FIGS. 1 and 2, the sleeve 22 is fixedly mounted, and if, with the individual parts 12 and 36 connected, the first individual part 12 is pulled (to the left in the illustration of FIG. 7), the clamp 26 is then drawn into the sleeve. The two jaws 28 and 30 thus close, such that they can clamp or tightly hold an element provided therebetween.

It is clear from the illustrations that the diameter of the wire 52, which comprises the connection body 38, is much smaller than the size of the eyelet opening 16. It is thus possible, for example in the connection state illustrated in FIG. 7, to pivot relative to one another the two individual parts 12 and 36 interconnected in this way.

Figure 8:
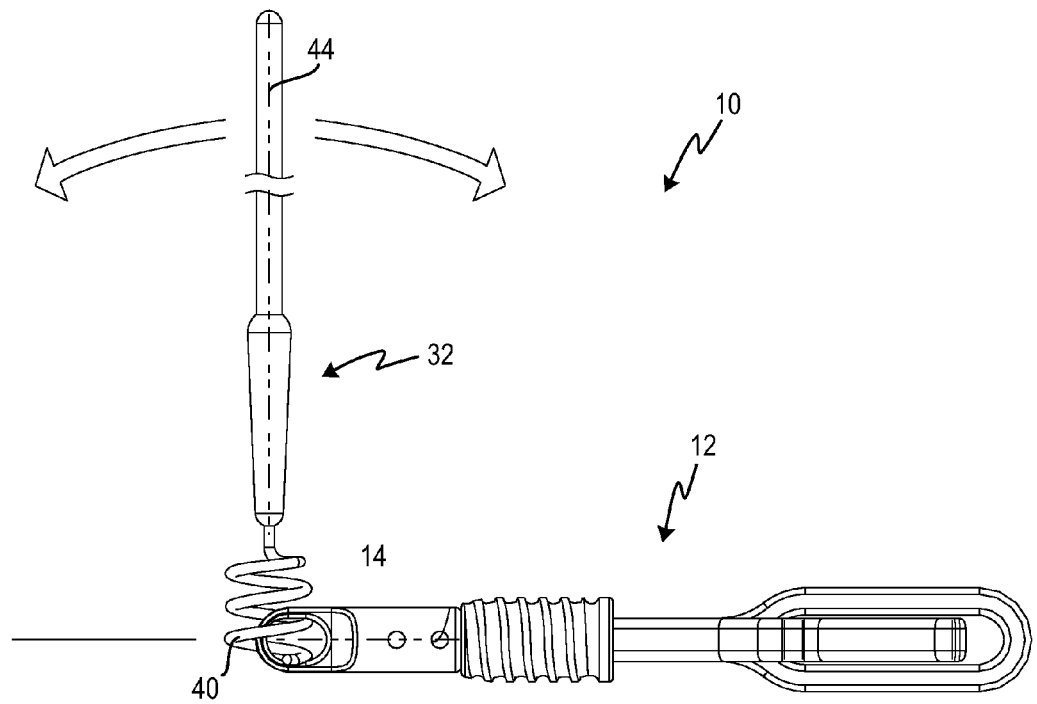
FIG. 8 shows a plan view of the assembly formed of the two individual parts with individual parts arranged at right angles to one another in the individual part plane.

It is illustrated in FIG. 8 that the second individual part 32 is pivoted for example through 90° in the device plane with respect to the straight extension from FIG. 7, this plane therefore corresponding here to the paper plane. As is shown in FIG. 8 by the two arrows, the second individual part 32 can be pivoted over a large region relative to the theoretically fixed first individual part 12. This increases the handling scope. It is also possible to provide the connection in such an angled position, that is to say the turns 40 may be screwed into or also unscrewed again from the eyelet 14 also in this angled orientation of the two individual parts 12 and 32 relative to one another.

This is then necessary in practical use for example if a number of clamps are already placed in a body and for example are pretensioned for clamping or holding, and if these are then to be recovered using the second individual part 32 along with the held tissue. Depending on the local conditions, it may be then possible for example that the eyelet 14 can be approached from the side, for example in the orientation illustrated in FIG. 8, and not in a linear orientation, as illustrated in FIG. 7.

This can already be seen for example from FIG. 6, that is to say it can be seen here that the connection can also be produced in a manner angled in this way.

Figure 9:
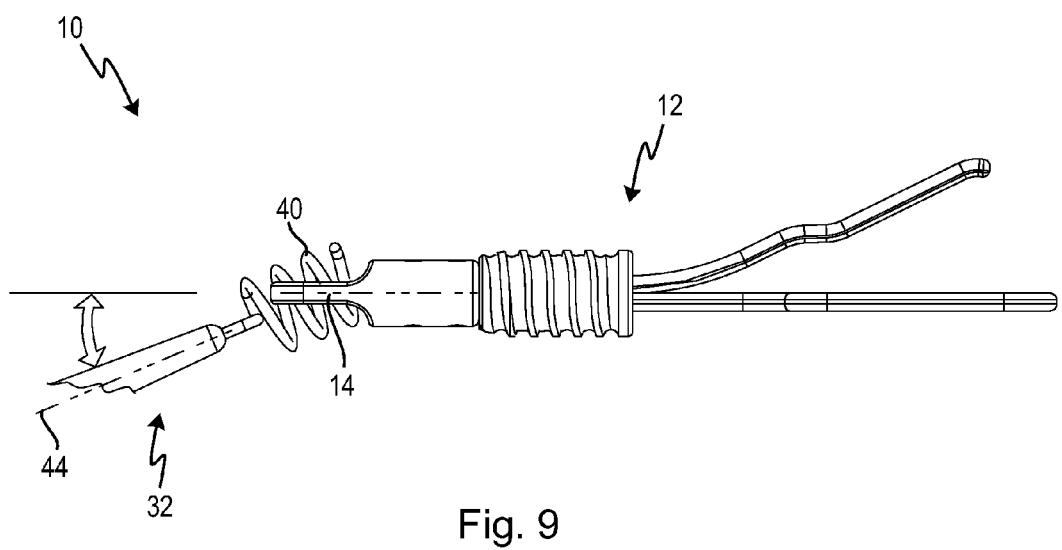
FIG. 9 shows a side view of the medical device with the second individual part pivoted out from the individual part plane.

A further degree of freedom is also illustrated in FIG. 9, that is to say the second individual part 32 cannot only be pivoted in this plane, as illustrated in FIG. 8, but can also be pivoted out from this plane, as is illustrated in FIG. 9 by the double-headed arrow.

This connection via the connection body 38 is therefore not only easily produced and released, but also allows the operator a high level of handling and manipulation freedom.

It was described before that the eyelet is provided on the clamp and that the corkscrew-like body is provided on the other individual part. This may also be reversed.

Figure 10:
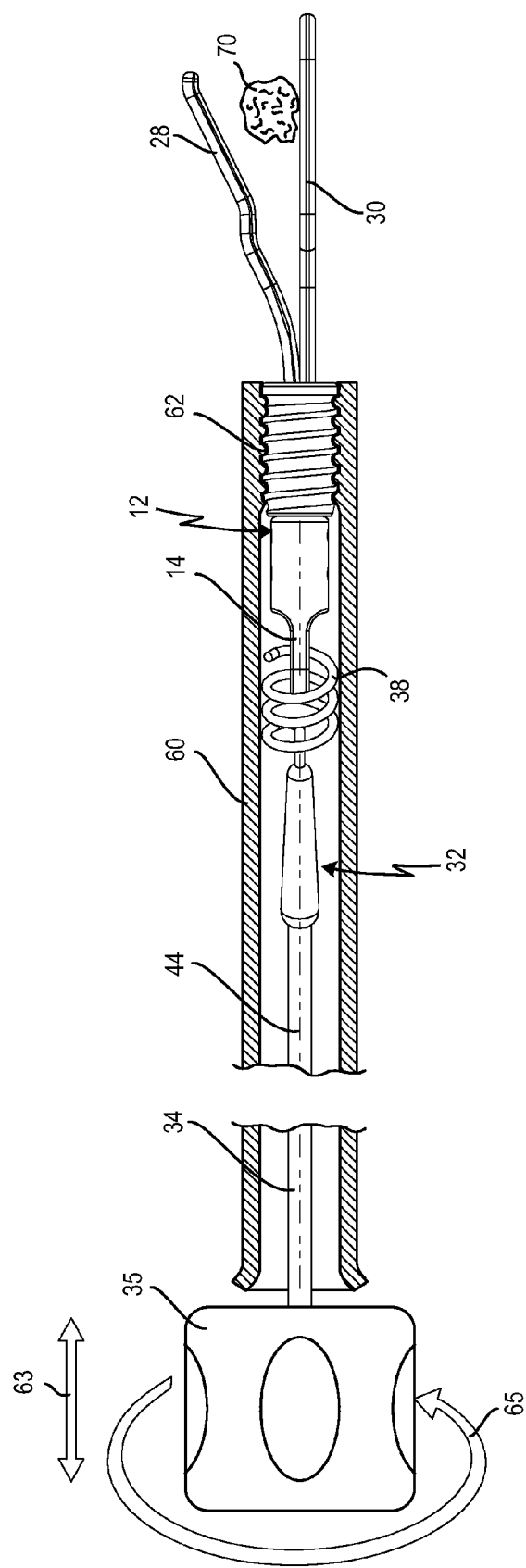
FIG. 10 shows a partly sectional side view of a device according to the invention, which is received in a hollow shaft for a minimally invasive intervention.

FIG. 10 illustrates how an assembly formed of the first individual part 12 and second individual part 32 is received in a hollow shaft 60 of a minimally invasive surgical instrument.

The hollow shaft 60, at one end, comprises an inner thread 62, into which the outer thread 24 of the screw 22 can be screwed.

The clamp 26 protrudes from the distal end, wherein the jaws 28 and 30 are spread here.

It is illustrated that the jaws 28 and 30 thus spread can be led to a tissue part 70 which is to be grasped by the clamp 26. The proximal end of the shaft 34 of the second individual part 32 is connected to a grip 35, which serves for the manipulation or handling of the second individual part 32. If the grip 35 is rotated for example, as is illustrated in FIG. 10 by the arrow 65, the assembly formed of the first individual part 12 and second individual part 32 rotates here in a clockwise direction, such that, for example as a result of this movement, the sleeve 22 can be screwed into the inner thread 62 of the hollow shaft 60.

If the first individual part 12 has already been installed accordingly beforehand in the hollow shaft 60 however, the second individual part 32, in order to produce the connection, can be inserted into the hollow shaft 60 from proximally to distally, and, as a result of rotation, the connection can then be produced between the turns 40 of the connection body 38 and the eyelet 14.

It can be seen from FIG. 10 that the previously illustrated embodiment of the connection body 38 is such that the outer contour line thereof corresponds to a cylinder, which is very favourable for the guidance of the connection body 38 in such a hollow shaft 60.

In other words, the connection body 38 can be well guided and therefore led in a targeted manner to the eyelet 14 and can then be screwed into the eyelet opening 16 as a result of a simple rotary movement, even if not under visual control. This facilitates the handling in this case particularly well.

In the mounted state illustrated in FIG. 10, the clamp 26 can now be drawn through the fixedly mounted sleeve 22 in the proximal direction, as is clear from the transition from FIG. 1 to FIG. 2, for example by moving the assembly from distally to proximally, as is illustrated by the arrow 63. In so doing, the jaws 28 and 30 close and then hold the tissue 70 tightly and reliably therebetween. Depending on the embodiment of the jaws 28 ad 30 and depending on the dimensions in the hollow shaft 60 and in the interior of the sleeve 22, the jaws 28 and 30 can be drawn fully into the hollow shaft 60, for example if they are to be introduced into a body in a manner already premounted minimally invasively in the hollow shaft 60. These two jaws 28 and 30 are then received in a protected manner in the interior of the hollow shaft 60 and can be discharged distally in the body. In so doing, the jaw 28 spreads and a tissue piece 70 may then be brought therebetween and tightly clamped by retracting the jaws 28.

Rather specific applications have been described above, however it is clear that such a connection between a first individual part 12 and a second individual part 32 can be used for other applications. It is also important that a first individual part 12 has an eyelet 14 into which the wire body of the connection body 38 of the second individual part 32 can be screwed, said wire body being wound in a spiralled or corkscrew-like manner.

Figure 11:
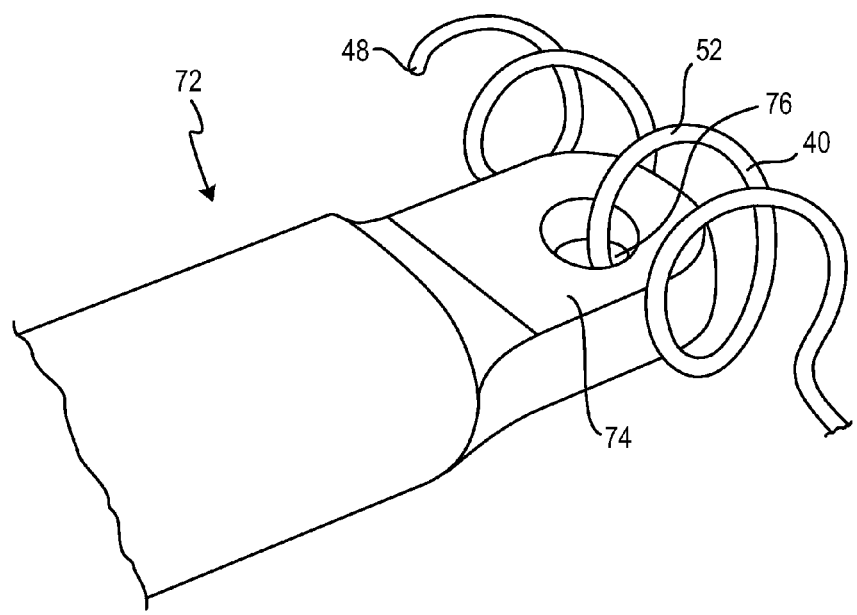
FIG. 11 shows an individual part having an eyelet with a small eyelet opening.

A further exemplary embodiment of an individual part 72 is illustrated in FIG. 11 and, at its outer end, comprises an eyelet 74 having an eyelet opening 76.

The eyelet opening 76 is relatively small compared with the exemplary embodiment illustrated previously in conjunction with FIGS. 1 and 2. The eyelet opening 76 is only insignificantly larger than the diameter of the wire 52 of the turns 40 of the further individual part. Only a single turn 40 is thus located in the eyelet opening 76. Even this connection is sufficiently reliable to prevent accidental release. At the same time, there are very large degrees of freedom in the angling and pivoting of the individual part comprising the turns 40 with respect to the individual part comprising this eyelet 74 having the small eyelet opening 76. In order to thread in the turns 40, the tip 48 thereof must then be positioned exactly at the small eyelet opening 76, which usually occurs under visual control.

Figure 12:
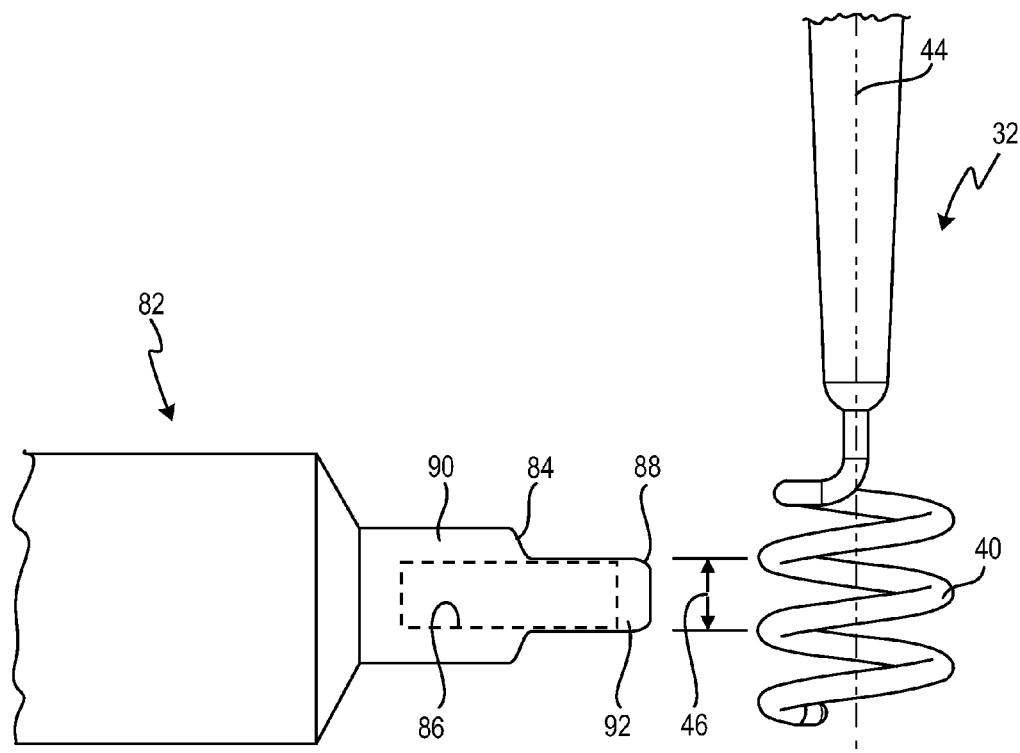
FIG. 12 shows an individual part having an eyelet of which the edge has different thicknesses or depths.

A further exemplary embodiment of an individual part 82 having an eyelet 84 is described in FIG. 12, in which a relatively large slot-shaped eyelet opening 86 is again contained, as is embodied in FIG. 1 by the eyelet opening in the form of the long oval 17.

Here, the edge 88 surrounding the eyelet opening 86 is stepped.

A first portion 90 has such a thickness or depth that is larger than the lead 46 of the turns 40 of the individual part 32 to be screwed into the eyelet opening 86.

The edge 88 has an outer second edge portion 92, which is thinner and of which the depth or thickness is slightly smaller than the lead 46 of the turns 40.

The turns 40 of the second individual part 32 can therefore be screwed into the eyelet opening 86 only in the region of the second edge portion 92.

This is just one possibility for a stepped edge, but can also be reversed such that the inner portion is thinner and the outer portion is wider. It may also be that the edge has just one indentation, such that the turns 40 can then be screwed in only in the region of the indentation.

Figure 13:
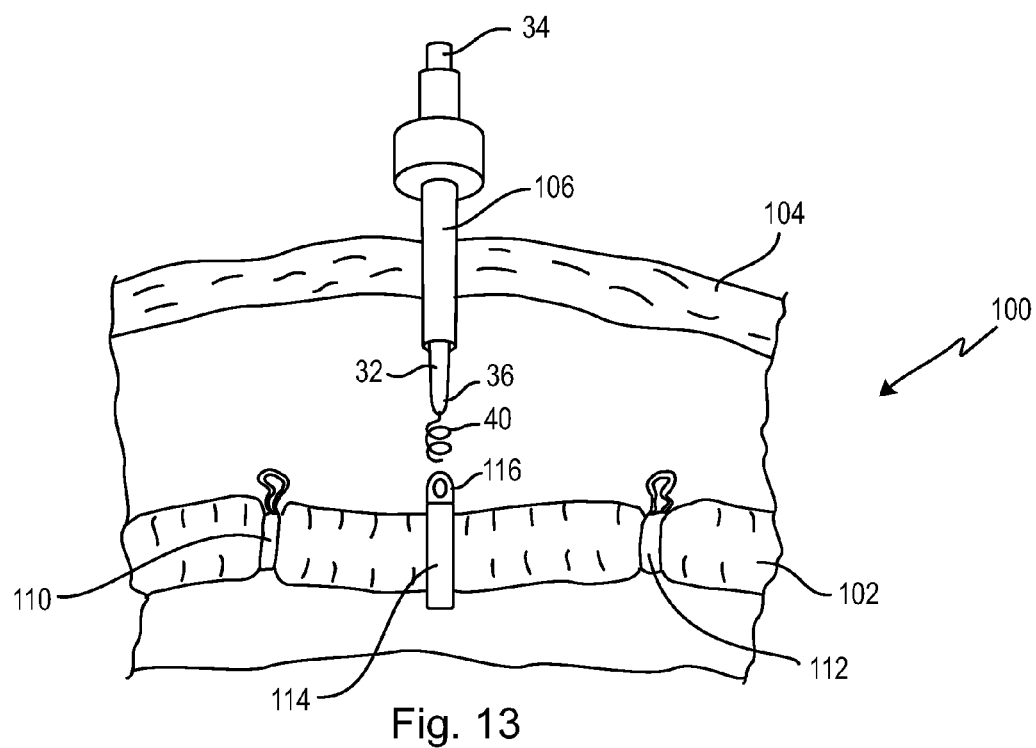
FIG. 13 shows a schematic view of a practical use of the instrument before the connection of the two individual parts.
Figure 14:
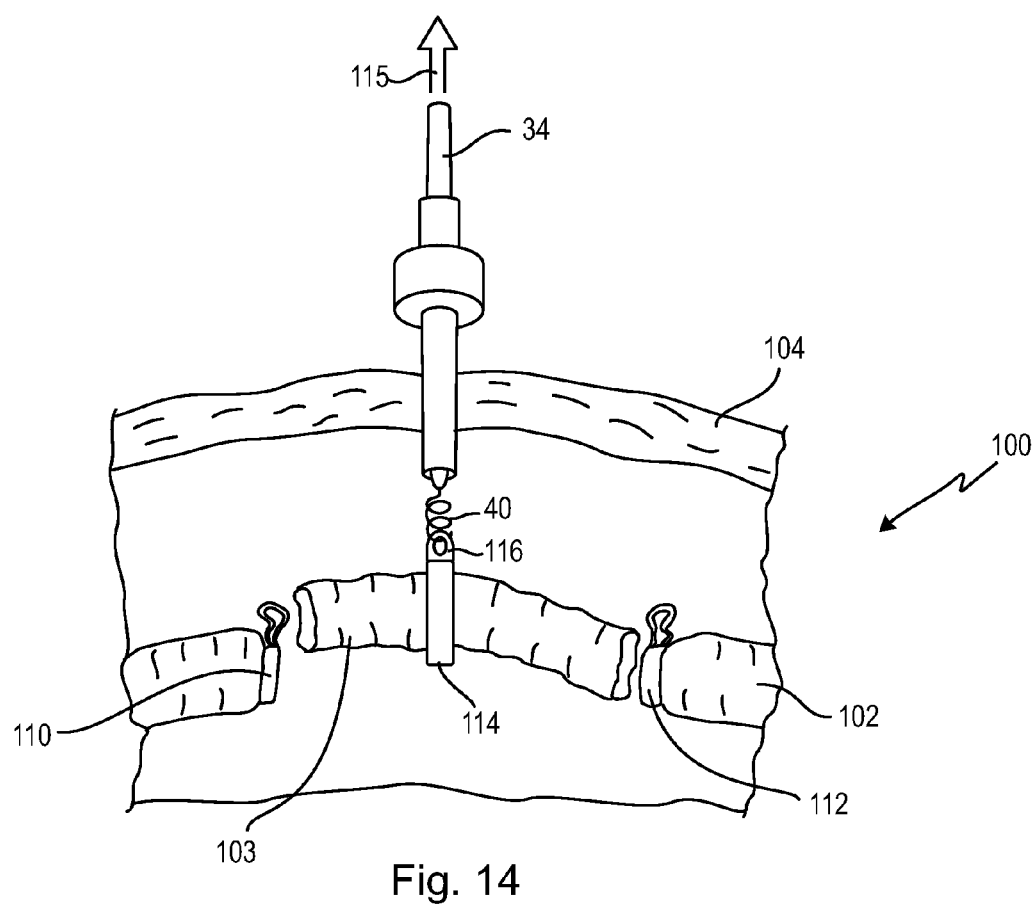
FIG. 14 shows an illustration corresponding to FIG. 12 once the two individual parts have been connected.

An example of a practical use of the medical instrument according to the invention is illustrated schematically in FIGS. 13 and 14.

FIG. 13 shows a partial section through a body 100, in the interior of which a vessel 102 is present. The vessel 102 may be a vein or a portion of the intestine, for example.

The skin 104 of the body 100 is pierced by a cannula 106, in which a second individual part 32 is received. Here, the shaft portion 36 with the turns 40 protrudes on the distal side beyond the end of the cannula 106.

The shaft 34 protrudes on the proximal side.

It is clear that the vessel 102 is gripped by a clamp 114, from which an eyelet 116 protrudes.

The clamp 114 is a clamp pretensioned towards closing and has been deposited beforehand on the vessel 102. The clamp thus grips around the vessel 102 in this region.

It can be inferred from FIG. 13 that the vessel 102 is constricted or, where applicable, even severed on either side of the clamp 114 by loops 112.

In FIG. 14 a situation is now illustrated in which the second individual part 32 has been slid distally through the cannula 106 until the turns 40 could be screwed into the eyelet 116 of the clamp 114. This can be performed under visual control by inserting an observation instrument, for example an endoscope, through the skin 104.

Once the connection between the second individual part 32 and the clamp 114 has been closed by screwing the turns 40 into the eyelet 116, the shaft 34 of the second individual part 32, as is illustrated in FIG. 14 by an arrow 115, can be drawn proximally. The piece 103 of the vessel 102 held by the clamp 114 is entrained and can be severed from the remaining vessel 102. FIG. 14 illustrates situation in which this piece 103 has already been severed.

The piece 102 thus gripped can now be recovered, for example removed from the body 110.

The two opposed ends in the region of the loops 110, 112 can then be joined together and interconnected again.

What is claimed is:

1. A medical instrument arrangement having two individual parts which can be releasably connected one to another via a hook/eyelet connection, comprising:
    a first individual part comprising an eyelet having a preformed eyelet opening fully surrounded by an eyelet edge having a thickness, and
    a second individual part comprising a connection body inserted into said eyelet opening,
    said connection body having turns wound in a corkscrew-like manner about a longitudinal axis of said second individual part,
    said turns turning at a radial distance from said longitudinal axis and around said longitudinal axis,
    two adjacent turns having an axial distance from one another that is at least equal to said thickness of said eyelet edge surrounding said eyelet, said turns of said connection body extend from a body of said second individual part,
    at least a section of one turn being screwed into said eyelet opening,
    said at least one turn engaging said eyelet to provide a connection between said two individual parts which allows a pulling or a pushing of said connected two individual parts by pulling or pushing one of said two connected individual parts, and allows a turning of said individual two parts in a direction of turning in said connection body when said turns completely cross said eyelet opening, wherein said first individual part is arranged as a medical instrument, and wherein said second individual part is arranged as a manipulator for the first individual part.

2. The arrangement of claim 1, wherein said connection body ends in an outer turn having an outer tip that runs approximately transversely to said longitudinal axis.

3. The arrangement of claim 1, wherein a helix angle of said turns is less than 45°.

4. The arrangement of claim 3, wherein said helix angle is within a range between 5° and 35°.

5. The arrangement of claim 4, wherein said helix angle is in a range between 10° and 20°.

6. The arrangement of claim 1, wherein said turns are each arranged at a same radial distance from said longitudinal axis over a length portion of said connection body.

7. The arrangement of claim 1, wherein an outer diameter of said first individual part and said second individual part are matched to one another in such a way that, in a connected state, both individual parts can be received in a hollow shaft suitable for minimally invasive surgery.

8. The arrangement of claim 1, wherein said turns are formed from a wire having a constant material diameter.

9. The arrangement of claim 1, wherein said first individual part comprises, at one end, a clamp having spreadable jaws, and, at an opposite end, said eyelet.

10. The arrangement of claim 9, wherein said jaws close when drawn into a hollow shaft, and wherein said second individual part is movable within a hollow shaft.

11. The arrangement of claim 1, wherein said eyelet is surrounded at least over a half of its outer circumference by an edge portion having said thickness.

12. The arrangement of claim 1, wherein said edge portion being formed as a U-shaped bow.

13. The arrangement of claim 1, wherein a size of said eyelet opening is selected in that only one turn can be threaded in.

14. The arrangement of claim 1, wherein a size of said eyelet opening is selected in such a way that a few turns can be threaded in.

15. The arrangement of claim 1, wherein said first individual part is having said thickness of said eyelet edge only in an area of said eyelet, but otherwise has a thicker size.

16. The arrangement of claim 1, wherein said connection body comprises an outer tip arranged as an integrally formed extension of an outer turn of said turns that is aligned with a general helical direction of said turns.

17. The arrangement of claim 1, wherein said eyelet is arranged as a flat elongated oval body having a main extension axis that is aligned with a central longitudinal axis of the first individual part.

18. A medical instrument having two individual parts which can be releasably connected one to another via a hook/eyelet connection, comprising a first individual part comprising an eyelet having a predefined eyelet opening fully surrounded by an eyelet edge having a thickness, and a second individual part comprising a connection body inserted into said eyelet opening, said connection body having turns wound in a corkscrew-like manner about a longitudinal axis of said second individual part, said turns turning at a radial distance from said longitudinal axis and around said longitudinal axis, two adjacent turns having an axial distance from one another that is at least equal to said thickness of said eyelet edge surrounding said eyelet, said turns of said connection body extend from a body of said second individual part, at least a section of one turn being screwed into said eyelet opening, said at least one turn engaging said eyelet to provide a connection between said two individual parts which allows a pulling or a pushing of said connected two individual parts by pulling or pushing one of said two connected individual parts, and allows a turning of said individual two parts in a direction of turning in said connection body when said turns completely cross said eyelet opening, wherein said first individual part comprises, at one end, a clamp having spreadable jaws, and, at an opposite end, said eyelet, and wherein said connection body comprises an outer tip arranged as an integrally formed extension of an outer turn of said turns.

19. The instrument of claim 18, wherein said outer tip extends in a circumferential direction that is aligned with a helical direction defined by said turns.

20. A medical instrument arrangement having two individual parts which can be releasably connected one to another via a hook/eyelet connection, comprising a first individual part comprising an eyelet having an eyelet opening defined and fully surrounded by an eyelet edge having a thickness, and a second individual part comprising a connection body inserted into said eyelet opening, said connection body having turns wound in a corkscrew-like manner about a longitudinal axis of said second individual part, said turns turning at a radial distance from said longitudinal axis and around said longitudinal axis, two adjacent turns having an axial distance from one another that is at least equal to said thickness of said eyelet edge surrounding said eyelet, said turns of said connection body extend from a body of said second individual part, at least a section of one turn being screwed into said eyelet opening, said at least one turn engaging said eyelet to provide a connection between said two individual parts which allows a pulling or a pushing of said connected two individual parts by pulling or pushing one of said two connected individual parts, and allows a turning of said individual two parts in a direction of turning in said connection body when said turns completely cross said eyelet opening, wherein said eyelet is arranged as a flat elongated oval body, and wherein said connection body comprises an outer tip arranged as an integrally formed aligned extension of an outer turn of said turns.

* * * * *